United States Patent
Cornmell et al.

(10) Patent No.: US 9,247,737 B2
(45) Date of Patent: Feb. 2, 2016

(54) METHOD FOR DISINFECTING A SURFACE

(71) Applicant: Rohm and Haas Company, Philadelphia, PA (US)

(72) Inventors: Robert J. Cornmell, Merseyside (GB); Megan A. Diehl, Line Lexington, PA (US); Stephen Golding, Merseyside (GB); John R. Harp, Knoxville, TN (US); Ian P. Stott, Merseyside (GB); Katherine M. Thompson, Merseyside (GB); Carol L. Truslow, Easton, PA (US)

(73) Assignee: Rohm and Haas Company, Philadelphia, PA (US)

( * ) Notice: Subject to any disclaimer, the term of this patent is extended or adjusted under 35 U.S.C. 154(b) by 33 days.

(21) Appl. No.: 14/363,432

(22) PCT Filed: Dec. 5, 2012

(86) PCT No.: PCT/EP2012/074416
§ 371 (c)(1),
(2) Date: Jun. 6, 2014

(87) PCT Pub. No.: WO2013/083590
PCT Pub. Date: Jun. 13, 2013

(65) Prior Publication Data
US 2015/0051297 A1 Feb. 19, 2015

Related U.S. Application Data

(60) Provisional application No. 61/567,360, filed on Dec. 6, 2011.

(30) Foreign Application Priority Data

Jun. 27, 2012 (EP) ..................................... 12173835

(51) Int. Cl.
*A61K 31/10* (2006.01)
*A01N 31/08* (2006.01)
*A61K 8/34* (2006.01)
*A61K 31/05* (2006.01)
*A61K 31/045* (2006.01)
*A61Q 11/00* (2006.01)
*A61Q 17/00* (2006.01)
*C11D 3/20* (2006.01)
*C11D 3/48* (2006.01)
*C11D 7/26* (2006.01)
*A01N 31/02* (2006.01)
*A01N 31/04* (2006.01)
*A61L 2/18* (2006.01)

(52) U.S. Cl.
CPC ................ *A01N 31/08* (2013.01); *A01N 31/02* (2013.01); *A01N 31/04* (2013.01); *A61K 8/342* (2013.01); *A61K 8/347* (2013.01); *A61K 31/045* (2013.01); *A61K 31/05* (2013.01); *A61L 2/18* (2013.01); *A61Q 11/00* (2013.01); *A61Q 17/005* (2013.01); *C11D 3/2037* (2013.01); *C11D 3/48* (2013.01); *C11D 7/261* (2013.01); *A61K 2800/592* (2013.01)

(58) Field of Classification Search
CPC ....... A01N 31/08; A01N 31/02; A01N 31/04; C11D 3/2037; C11D 7/261; C11D 3/48; A61L 2/18; A61Q 11/00; A61Q 17/005; A61K 8/342; A61K 31/045; A61K 8/347; A61K 3/05; A61K 2800/592
USPC .......................................................... 514/731
See application file for complete search history.

(56) References Cited

U.S. PATENT DOCUMENTS

| | | | |
|---|---|---|---|
| 6,436,342 B1 * | 8/2002 | Petri | A01N 59/00 422/28 |
| 2003/0180349 A1 | 9/2003 | Franklin | |
| 2005/0014827 A1 | 1/2005 | Schur | |
| 2008/0118591 A1 | 5/2008 | Natsch | |
| 2008/0194518 A1 | 8/2008 | Mookerjee et al. | |

FOREIGN PATENT DOCUMENTS

| | | | | |
|---|---|---|---|---|
| WO | WO01/79409 | * | 10/2001 | ............... C11D 3/48 |
| WO | 2006/053458 A1 | | 5/2006 | |
| WO | WO2008/035101 | * | 3/2008 | ............. A01N 25/04 |
| WO | 2008/126057 A2 | | 10/2008 | |
| WO | 2010/046238 A1 | | 4/2010 | |
| WO | 2010/070215 A1 | | 6/2010 | |

* cited by examiner

*Primary Examiner* — T. Victor Oh
(74) *Attorney, Agent, or Firm* — Kenneth Crimaldi

(57) ABSTRACT

The present invention relates to a method for disinfection involving an antimicrobial composition. It particularly relates to an antimicrobial method for personal cleaning, oral care or hard surface cleaning applications. It was found that compositions comprising thymol, acyclic terpene alcohols and a carrier provide synergistic antimicrobial action in a method for disinfection. In a preferred aspect the composition also comprises 1 to 80%-wt of one or more surfactants.

3 Claims, No Drawings

METHOD FOR DISINFECTING A SURFACE

FIELD OF THE INVENTION

The present invention relates to a method for disinfection involving an antimicrobial composition. It particularly relates to a method for disinfecting a hard surface or a surface in or on the human body.

BACKGROUND TO THE INVENTION

Sanitising and disinfecting soap or cleaning compositions are of great benefit to individuals, since proper use generally may reduce the number of germs and pathogens the individual is exposed to. Thus, such compositions and methods involving such compositions may for instance play an important role in reducing the occurrence and spread of infectious diseases.

Sanitising and disinfecting soap compositions comprising chlorine-based antimicrobial agents such as triclosan are known. Such compositions require a rather long contact time to provide efficacious antimicrobial action. In practice, users, in particular children, do not spend a long time on cleansing and as a result cleaning with such compositions does not provide adequate prevention from surface or topical infection or adequate protection against diseases. The user, in spite of cleaning his hands, is generally likely to end up with relatively inadequate bacterial removal from his skin. Therefore, he may cause contamination of further animate and/or inanimate surfaces, and contribute to the spreading of pathogens and consequent diseases. Users in general and children in particular who wash contaminated hands before meals with slow-acting antimicrobial compositions for relatively short time are at risk of contracting diseases.

Similarly in the area of hard surface cleaning, e.g. cleaning of floors, table tops or utensils, the antimicrobial actives in the compositions are in contact with the substrate for less than a few minutes after which the surface is either wiped off or rinsed with water. These short time scales of cleaning action are ineffective in providing the desired benefit since most known antimicrobials commonly used in such products take many minutes to hours to provide the desired kill of microbes.

Therefore, there is a need of providing a method involving a composition that—upon application—provides relatively more efficacious antimicrobial action during a relatively short cleaning period, preferably about 30 seconds or less, and more preferably about 15 seconds or less.

A well-established class of antimicrobially active compounds are phenolic compounds [P A Goddard and K A McCue in "Disinfection, Sterilisation and Preservation", ed, S S Block 5$^{th}$ edition, Lippincott, Williams and Wilkins, Philadelphia, 2001 pp, 255-282]. However, not every phenolic compound is suitable as an antimicrobial agent. Moreover, many phenols—even if they are antimicrobially active—may exhibit undesirable side-effects, such as corrosiveness, malodour and irritating or sensitising effects when applied on the human or animal skin.

A particular problem of thymol is that its presence in a formulation is generally well-perceptible due to its olfactory properties. Although the latter may—at least to some extent—be appreciated in certain fragrance compositions, it is considered too intense by some users when applied at concentrations efficacious in rapid disinfection. Additionally, a lower concentration of odoriferous compounds including thymol or the availability of antimicrobial compounds that are less or not odoriferous allows greater flexibility to the manufacturer in providing alternative scents to his composition at lower doses. Hence there is a need to provide alternative antimicrobial compositions and methods that preferably require lower concentrations of thymol and/or have a more acceptable sensory profile.

WO 2010/046238 A1 describes an effective antimicrobial composition which provides rapid kill of pathogenic bacteria and which comprises 0.01 to 5% by weight of thymol, 0.01 to 5% by weight of terpineol and a carrier. WO 2010/046238 A1 also discloses a method for rapidly disinfecting a surface including the step of applying the above composition to the surface.

WO 06/053458 is directed at providing bactericidal formulations containing perfume ingredients that have a rapid bactericidal effect against Gram-negative and preferably also against Gram-positive bacteria and a method for providing these formulations. The document discloses a formulation comprising (a) at least 0.2% (w/v) of one or more selected perfume ingredients, (b) 4% to 20% (w/v) of a hydrotrope and (c) 0.1% to 9% (w/v) of one or more selected surfactants. It also discloses that certain perfume ingredients have a rapid (30 s) bactericidal effect on gram-negative bacteria.

FR 2 697 133 discloses biocidal and/or biostatic compositions, comprising mono-oxygenated sesquiterpenes of general formula $C_{15}H_xO$, wherein x is between 20 and 26 and aromatic compounds.

WO 01/79409 discloses a process of disinfecting a hard surface with a composition comprising cinnamon oil and/or an active thereof. Preferably, the composition comprises a ternary essential oil and/or active thereof system consisting of cinnamon oil and/or an active thereof, a first additional essential oil and/or active thereof, preferably thymol; and a second additional essential oil and/or active thereof, preferably geraniol.

WO 2008/035101 discloses a disinfectant emulsion composition having a continuous phase having dissolved therein a first antimicrobial agent and a discontinuous phase having dissolved therein a second antimicrobial agent. A method of cleansing the hands of a human subject with the emulsion is also disclosed.

Despite the general availability of antimicrobial compounds, compositions, and methods, there remains a continuous need to find alternative antimicrobial methods, and compositions and/or active compounds that are suitable for use in such methods, In particular, alternative methods providing fast antimicrobial action remain highly desirable in view of current consumer habits. In case such alternatives are based on alternative compositions, they may reduce the dependency on current raw materials. Moreover, in the field of antimicrobials, the availability of alternatives may reduce the risk of development of microbial resistance or insensitivity to particular antimicrobial compounds.

In addition, there is a continued need to reduce the total amount of active ingredients required in such an antimicrobial composition for use in an antimicrobial method. This need may for instance be driven by the desire for cost-efficiency, because such compositions are particularly relevant to developing countries. Moreover, reducing the amounts may also be beneficial for environmental reasons. In view of the above-observed problems and drawbacks of the prior art, it is an object of the present invention to provide a method for sanitising and/or disinfecting, in particular of surfaces.

It is a further object of the invention to provide a method for disinfection with a reduced disinfection time. More specifically, it is an object of the invention to provide a method, wherein the disinfection time of the method is less than 300 seconds, preferably less than 60 seconds, and more preferably less than 15 seconds.

In particular, it is an object of the invention to provide a method for disinfection that gives improved disinfection during cleansing of surfaces, in particular hard surfaces, or surfaces of the human body; such as the skin and the oral cavity.

It is another object of the invention to provide a method for disinfection requiring an antimicrobial composition involving a lower dose of antimicrobial compounds.

Similarly, it is an object of the present invention to provide a method for disinfection requiring an antimicrobial composition in which the olfactory contribution of the antimicrobially active compounds is reduced or in which the active compound contributes to providing a consumer-acceptable or even consumer-appreciated scent.

SUMMARY OF THE INVENTION

We have now found that one or more of the above objects are met by the present invention. Thus, we have found that compositions comprising selected acyclic terpene alcohols and thymol provide synergistic antimicrobial action when applied in a method according to the present invention. Upon application, such compositions provide similar or more efficacious anti-microbial action, at similar or even lower concentrations when compared to thymol and alpha-terpineol. In particular, we found that upon application according to this invention of combinations of acyclic terpene alcohols and thymol, very fast antimicrobial action is obtained. For instance, we found that complete microbial inactivation could be effected with compositions according to the present invention after a contact time of only 15 seconds.

By virtue of the enhanced antimicrobial efficacy of acyclic terpene alcohols together with thymol, the reduction of the required amount of thymol advantageously also contributes to a reduction of the olfactory disadvantages associate with the presence of larger amounts of thymol.

Accordingly, in a first aspect the invention provides a method of disinfecting a surface comprising the steps of
  a. applying to the surface an antimicrobial composition comprising
    i. 0.001 to 5% by weight of thymol,
    ii. 0.001 to 5% by weight of one or more acyclic terpene alcohols, and
    iii. a carrier; and
  b. removing the composition from the surface,
wherein the one or more acyclic terpene alcohols have the following structure

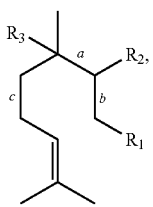

wherein
  the bonds (a), (b) and (c) are single or double bonds, whereby at most one of the bonds (a), (b) and (c) is a double bond, and whereby said double bond is not adjacent to the hydroxy group, and
  $R_1$, $R_2$ and $R_3$ are selected from hydrogen and hydroxy, whereby exactly one of $R_1$, $R_2$ and $R_3$ is hydroxy, with the proviso that $R_3$ is absent if bond (a) is a double bond;

and wherein the step of removing the composition is started less than 2 minutes after commencement of the step of applying the composition on the surface.

In a second aspect, the invention provides the use of a composition for improved hygiene, whereby the composition comprises
  i. 0.001 to 5% by weight of thymol,
  ii. 0.001 to 5% by weight of one or more acyclic terpene alcohols, and
  iii. a carrier; and
wherein the one or more acyclic terpene alcohols have the following structure,

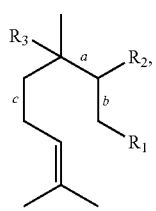

wherein
  the bonds (a), (b) and (c) are single or double bonds, whereby at most one of the bonds (a), (b) and (c) is a double bond, and whereby said double bond is not adjacent to the hydroxy group, and
  $R_1$, $R_2$ and $R_3$ are selected from hydrogen and hydroxy, whereby exactly one of $R_1$, $R_2$ and $R_3$ is hydroxy, with the proviso that $R_3$ absent if bond (a) is a double bond.

DETAILED DESCRIPTION OF THE INVENTION

For the avoidance of doubt any feature of one aspect of the present invention may be utilised in any other aspect of the invention. The word "comprising" is intended to mean "including" but not necessarily "consisting of" or "composed of." Thus, the term "comprising" is meant not to be limiting to any subsequently stated elements but rather to optionally also encompass non-specified elements of major or minor functional importance. In other words, the listed steps or options need not be exhaustive. Whenever the words "including" or "having" are used these terms are meant to be equivalent to "comprising" as defined above, it is noted that the examples given in the description below are intended to clarify the invention and are not intended to limit the invention to those examples per se.

Except in the examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

Throughout this description, the term disinfection refers to reduction of the number of viable microorganisms in a given medium or on a given surface by physical or chemical means. Typically, disinfection involves the destruction or inactivation of said microorganisms. Both animate and inanimate media and surfaces are contemplated.

The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mould), bacteria and algae.

The method of the present invention preferably is a non-therapeutic method, and more preferably a method for cleaning surfaces of human body including skin, hair or oral cavity or for hard surface cleaning applications.

Method According to the Invention, Step a.

According to the first aspect, the invention relates to a method of disinfecting a surface. The method comprises the step of applying an antimicrobial composition on to the surface.

Preferably, the surface is skin. Thus, for example, a surface like the hands, face, body, or the oral cavity is contacted with the composition of the invention. If the surface is a surface of a human or animal body, the method preferably is a non-therapeutic method of disinfecting a surface. Alternatively, the surface is any hard surface. Typically, such hard surfaces are surfaces that commonly require cleaning and preferably also require sanitisation or disinfection. Such surfaces may be found in many household or industrial environments, and may include for example kitchen and bathroom surfaces, table tops, floors, walls, windows, utensils, cutlery, and crockery. Such surfaces may be made from many different materials, including for instance plastics, wood, metal, ceramics, glass, concrete, marble, and painted surfaces.

The composition may be applied to the surface by any suitable means known to the skilled person. For instance, a suitable means may be pouring, dropping, spraying or wiping in case of liquid compositions.

Preferably, the method includes diluting or dissolving the composition with a suitable solvent, preferably water, before or whilst applying the composition to the surface. Such dissolving is preferred in particular in case the composition is a solid composition, Alternatively, solid compositions may also be directly spread, rubbed, or sprayed, e.g. in the form of a powder.

The antimicrobial composition comprises
i. 0.001 to 5% by weight of thymol,
ii. 0.001 to 5% by weight of one or more acyclic terpene alcohols, and
iii. a carrier.

Acyclic Terpene Alcohols

The antimicrobial composition according to the invention comprises 0.001 to 5% by weight of one or more acyclic terpene alcohols. The composition comprises preferably 0.005 to 4.5 wt-%, more preferably 0.01 to 4 wt-%, even more preferably 0.02 to 3 wt-%, yet more preferably 0.03 to 2 wt-%, still more preferably 0.04 to 1 wt-%, even more preferably 0.05 to 0.75 wt-% and still more preferably 0.1 to 0.6 wt-% of the one or more acyclic terpene alcohols. In compositions intended to be diluted before application, the minimum preferred concentrations of the one or more acyclic terpene alcohols can be higher. For example, when washing hands with water and a composition according to the invention, the lather produced, typically is a 50 wt % dilution of the original composition. Similarly, in body wash situations, soap bars or soap liquids are typically diluted until about 8 wt % soap in water, corresponding to an approximately tenfold dilution of the product. Therefore, compositions according to the invention intended for dilution upon use preferably comprise 0.05 to 4.5 wt-%, more preferably 0.1 to 4 wt-%, even more preferably 0.2 to 3 wt-%, still more preferably 0.4 to 1 wt-%, and still more preferably 0.5 to 1 wt-% of the one or more acyclic terpene alcohols. Thus, the concentration of the one or more acyclic terpene alcohols in the antimicrobial composition is preferably such that when the composition is diluted or dissolved with a suitable medium during use, the concentration in the diluted or dissolved mixture is still sufficient to be antimicrobially efficacious.

The acyclic terpene alcohol can be a single compound or can be a mixture of the acyclic terpene alcohols as detailed below. In certain preferred embodiments, mixtures of acyclic terpene alcohols are preferred, since such mixtures may show increased antimicrobial activity against a wider range of microbes. On the other hand, for reasons including e.g., control over the formulation, it is preferred that in case the composition according to the invention comprises a mixture of such acyclic terpene alcohols, the mixture preferably comprises at least 30%, more preferably at least 50%, even more preferably at least 70% and still more preferably at least 90% by weight of one acyclic terpene alcohol with respect to the total weight of the acyclic terpene alcohols.

At concentration ranges of the acyclic terpene alcohols below the lower concentration limits of the acyclic terpene alcohols, the desired fast acting antimicrobial kinetics in combination with thymol would not be met. At concentrations higher than the higher preferred concentrations of acyclic terpene alcohols, when in combination with thymol, while the kinetics of action would not be compromised, the present inventors have found that unlike in therapeutic/pesticidal/herbicidal applications where sensorial aspects are not critical, in the present invention, which preferably relates to personal cleaning, oral care or hard surface cleaning applications, the product is in contact with hands, mouth or other body parts, the sensorial aspects including smell and skin feel would be compromised.

The one or more acyclic terpene alcohols have the following structure:

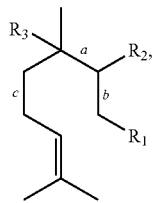

wherein $R_1$, $R_2$ and $R_3$ are selected from hydrogen and hydroxy, whereby exactly one of $R_1$, $R_2$ and $R_3$ is hydroxy, with the proviso that $R_3$ is absent if bond (a) is a double bond. The bonds (a), (b) and (c) are single or double bonds, whereby at most one of the bonds (a), (b) and (c) is a double bond, and whereby said double bond is not adjacent to the hydroxy group. Therefore, if for example $R_1$ is selected to be the hydroxy group, both $R_2$ and $R_3$ are hydrogen, bond (b) is a single bond, and bonds (a) and (c) can be single bonds or one of (a) and (c) can be a double bond.

Several non-limiting examples of the structures of the one or more acyclic terpene alcohols according to the present invention are provided in Table 1.

TABLE 1

| | |
|---|---|
| (S)-3,7-dimethylocta-1,6-dien-3-ol | 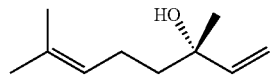 |
| (R)-3,7-dimethylocta-1,6-dien-3-ol | 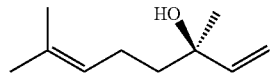 |

TABLE 1-continued

| | |
|---|---|
| (E)-3,7-dimethylocta-2,6-dien-1-ol | 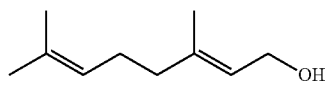 |
| (Z)-3,7-dimethylocta-2,6-dien-1-ol | 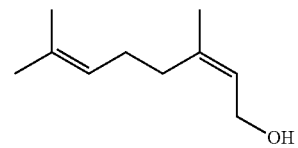 |
| 3,7-dimethyl-6-octen-1-ol | 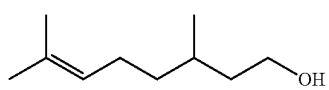 |

It is preferred that the one or more acyclic terpene alcohols are selected from the group consisting of linalool, geraniol, nerd, and citronellol.

Linalool is 3,7-dimethylocta-1,6-dien-3-ol. It exists as two stereoisomers, (S)-(−)-linalool, which is (S)-3,7-dimethylocta-1,6-dien-3-ol and (R)-(+)-linalool, which is (R)-3,7-dimethylocta-1,6-dien-3-ol. Mixtures of these isomers are contemplated too. Geraniol is (E)-3,7-dimethylocta-2,6-dien-1-ol. Nerol is (Z)-3,7-dimethylocta-2,6-dien-1-ol. Mixtures of geraniol and nerol are also known as citrol and are also contemplated. Citronellol is 3,7-dimethyl-6-octen-1-ol. The two stereoisomers of citronellol commonly occur as mixtures in nature. Therefore (R)-3,7-dimethyl-6-octen-1-ol, (S)-3,7-dimethyl-6-octen-1-ol, and mixtures thereof are equally preferable.

Preferably the one or more acyclic terpene alcohols are selected from the group consisting of linalool, geraniol, and citronellol and more preferably, from the group consisting of linalool and geraniol. This preference, which is for instance relevant to embodiments directed to disinfection of the skin, is based on the favourable toxicological profile of these compounds. It is even more preferred that the acyclic terpene alcohol is geraniol since geraniol displays the fast synergistic antimicrobial action upon combination with thymol at relatively low concentrations.

In case the carrier or the dissolution medium during later application is water-based, it can be advantageous if the one or more acyclic terpene alcohols are sufficiently water-soluble. The acyclic terpene alcohols are sufficiently water-soluble if they are soluble to at least the minimum concentration required in the antimicrobial composition according the invention.

Advantageously, some compounds according to the invention have a weaker odour, when compared to that of terpineol, or an odour which can be more appreciable to the consumer, when dosed into the compositions according to the invention at efficacious levels. This benefit especially applies to for instance geraniol, linalool, and citronellol.

Mixtures of preferred acyclic terpene alcohols are also preferred.

Without wishing to be bound by theory, it is believed that the synergistic mode of antimicrobial action of the acyclic terpene alcohols according to the present invention in combination with thymol is similar for the different respective acyclic terpene alcohols.

Suitable acyclic terpene alcohols according to the present invention may be commercially sourced, obtained from natural sources or via synthetic chemical methods. Such sources and methods are generally well-known to the person skilled the art, and can be found, for example in KG Pahlbusch, F J Hammerschmidt et al, "Flavors and Fragrances", Ullmann's Encyclopedia of industrial Chemistry, Vol 15, P 74, online edition, 2003, Wiley VCH, DOI: 10.1002/4356007.a11_141.

Thymol

Thymol has the following structure:

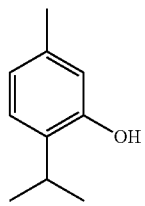

Thymol is also known as 2-isopropyl-5-methylphenol.

The antimicrobial composition used in the method of disinfecting according to the invention comprises 0.001 to 5% by weight of thymol. The composition comprises preferably 0.005 to 4.5 wt-%, more preferably 0.01 to 4 wt-%, even more preferably 0.02 to 3 wt-%, yet more preferably 0.03 to 2 wt-%, still more preferably 0.04 to 1 wt-%, still more preferably 0.05 to 0.75 wt-% and even more preferably 0.1 to 0.5 wt-% of thymol. In compositions intended to be diluted before application, the minimum preferred concentrations of the thymol can be higher, for the same reasons as for the acyclic terpene alcohols. Therefore, compositions according to the invention intended for dilution upon use preferably comprise 0.05 to 4.5 wt-%, more preferably 0.1 to 4 wt-%, even more preferably 0.2 to 3 wt-%, still more preferably 0.4 to 1 wt-%, and still more preferably 0.5 to 1 wt-% of the thymol. Any of the concentrations ranges for the thymol is preferably combined with any of the concentration ranges for the one or more acyclic terpene alcohols specified above. Therefore, the antimicrobial composition for example comprises:

a. 0.01 to 0.4% by weight of thymol;
b. 0.05 to 1% by weight of the one or more acyclic terpene alcohols.

The preferred concentrations ranges of the thymol are important for the same reasons as the preferred concentration ranges of the one or more acyclic terpene alcohols in meeting the desired fast acting antimicrobial kinetics while not being sensorially unpleasant when used in products for personal cleaning, oral care or hard surface cleaning applications.

Thymol may be added to the antimicrobial composition in purified form. However, thymol is compound that is naturally present in many plant species. Therefore, alternatively, plant oils or plant extracts derived from such thymol-containing plant species can be added to the antimicrobial composition, while ensuring that thymol is present in the desired concentration in the composition of the present invention. For example, thyme oil or thyme extract naturally comprise thymol. Thyme oil or thyme extract is obtained from the thyme plant. Thyme plant refers to a plant belonging to the genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus aigeriensis, Thymus serpyllum, Thymus pulegoide*, and *Thymus citriodorus*.

Carrier

The antimicrobial composition comprises a carrier. The carrier is preferably selected from the group consisting, of water, oil, solvent, inorganic panic date material, starch, air and mixtures thereof. The carrier is preferably from 0.1 to 99% by weight of the composition. The antimicrobial composition may be in form of a solid, liquid, gel, paste or soft solid and the carrier may be selected by a person skilled in the art depending on the format of the antimicrobial composition.

Examples of inorganic particulate materials include clay, talc, calcite, dolomite, silica, and aluminosilicate. Examples of oils include mineral oils, oils of biological origin (e.g. vegetable oils), and petroleum-derived oils and waxes. The oils of biological origin are preferably triglyceride-based. Preferably, the carrier oil is not a perfume oil. Thus, the carrier oil preferably does not substantially contribute to the odour of the composition, more preferably it does not contribute to that odour. Examples of solvents, include alcohols, ethers and acetone. The starch may be natural starch obtained from food grains or may be a modified starch.

In certain preferred embodiments, suitable solvents include, for example, water; glycols, including ethylene glycol, propylene glycol; diethylene glycol, dipropylene glycol, polyethylene glycol, and polypropylene glycol, glycol ethers, alcohols, such as methanol, ethanol, propanol, phenethyl alcohol and phenoxypropanol, ketones, including acetone and methyl ethyl ketone; esters, including ethyl acetate, butyl acetate, triacetyl citrate, and glycerol triacetate carbonates, including propylene carbonate and dimethyl carbonate; and mixtures thereof. It is preferred that the solvent is selected from water, glycols, glycol ethers, esters and mixtures thereof. Alternatively, it is preferred that the carrier comprises water, ethanol, propanol, isopropanol, ethylene propylene glycol, diethylene glycol or a mixture thereof. In certain preferred embodiments, suitable solid carriers include, for example, cyclodextrin, silicas diatomaceous earth, waxes, cellulosic materials, alkali and alkaline earth (e.g., sodium, magnesium, potassium) metal salts (e.g., chloride, nitrate, bromide, sulfate) and charcoal.

Air can for instance be used as a carrier when the acyclic terpene alcohols according to the invention and/or the thymol are atomised or otherwise dispersed as a fine mist.

Particularly preferred carriers are water or oil/solvent and even more preferred is a carrier that is a mixture of water and oil. Thus, in many of the envisaged applications like personal care/washing, oral care and hard surface cleaning, the antimicrobial composition may be formulated with either an aqueous base or a oil/solvent base. Compositions with an aqueous base (water being the carrier), may also for instance be products in gel format. Compositions with a purely oil/solvent base may for instance be products in anhydrous stick form or propellant-containing products.

Thus, the antimicrobial composition may for instance, preferably be an antimicrobial anhydrous stick personal care composition on a purely oil/solvent base wherein the composition has a water content of less than 0.01% by weight, and wherein the composition preferably is free of water. Alternatively, the antimicrobial composition may for instance, preferably be an antimicrobial propellant-drivable personal care composition, also comprising a propellant. Air can also be used as propellant, for instance in the form of compressed or liquefied air.

However, the most preferred product format has an emulsion base (water and/or oil being the carrier) or is capable of forming an emulsion upon dilution, e.g. soap products in liquid, solid, lotion or semisolid form for hand wash, face wash, body wash, or shaving applications; toothpaste/dentifrices for oral care applications or products for hard surface cleaning in bars or liquids form. If the product comprises an emulsion base, it preferably also comprises one or more surfactants as described below.

Surfactants

The antimicrobial composition according to the invention preferably comprises from 1 to 80% by weight of one or more surfactants. Surfactants may for instance advantageously contribute to the cleaning efficacy or the formulation stability of a composition.

Thus, the antimicrobial composition for use in the method of disinfecting according the invention preferably comprises
   a. 0.001 to 5% by weight of thymol,
   b. 0.001 to 5% by weight of the one or more acyclic terpene alcohols according to the invention,
   c. a carrier, and
   d. from 1 to 80% by weight of one or more surfactants.

It is particularly preferred that the antimicrobial composition comprises from 1 to 80% by weight of one or more surfactants in combination with the one or more acyclic terpene alcohols, and the thymol at their more preferred concentrations as specified above.

In general, the surfactants may be chosen from the surfactants described in well-known textbooks like "Surface Active Agents" Vol. 1, by Schwartz 8, Perry, Interscience 1949, Vol. 2 by Schwartz. Perry & Berch, Interscience 1958, and/or the current edition of "McCutcheon's Emulsifiers and Detergents" published by Manufacturing Confectioners Company or in "Tenside-Taschenbuch", H, Stache, 2nd Edn., Carl Hauser Verlag, 1981; "Handbook of industrial Surfactants" (4th Edn.) by Michael Ash and Irene Ash; Synapse information Resources, 2008, Any type of surfactant, i.e. anionic, cationic, nonionic, zwitterionic or amphoteric can be used. Preferably, the one or more surfactants are anionic, nonionic, or a combination of anionic and nonionic surfactants. More preferably, the one or more surfactants are anionic.

A particularly preferred surfactant is soap. Soap is a suitable surfactant for personal washing applications of the antimicrobial composition of the invention. The soap is preferably $C_6$-$C_{24}$ soap, more preferably a $C_{10}$-$C_{20}$ soap and most preferably $C_{12}$-$C_{16}$ soap. The soap may or may not have one or more carbon-carbon double bonds or triple bonds. The cation of the soap can for instance be an alkali metal, alkaline earth metal or ammonium. Preferably, the cation of the soap is selected from sodium, potassium or ammonium. More preferably the cation or the soap is sodium or potassium.

The soap may be obtained by saponifying a fat and/or a fatty acid. The rats or oils may be fats or oils generally used in soap manufacture, such as tallow, tallow stearines, palm oil, palm stearines, soya bean oil, fish oil, castor oil, rice bran oil, sunflower oil, coconut oil, babassu oil, palm kernel di, and others. In the above process the fatty acids are derived from oils/fats selected from coconut, rice bran, groundnut tallow, palm, palm kernel, cotton seed, soyabean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources. Other similar mixtures, such as those from palm oil and those derived from various animal tallow and lard are also included.

A typical fatty acid blend consists of 5 to 30%-wt coconut fatty acids and 70 to 95%-wt fatty acids ex hardened rice bran oil. Fatty acids derived from other suitable oils/fats such as groundnut, soybean, tallow, palm, palm kernel, etc. may also be used in other desired proportions. The soap, when present in solid forms of the present invention, is preferably present in an amount of 30 to 80%, more preferably from 50 to 80%, and even more preferably 55 to 75% by weight of the composition. The soap, when present in liquid forms of the composition is preferably present in 0.5 to 20%, more preferably from 1 to 10% by weight of the composition.

Other preferred surfactants are fatty acid glycinates and fatty amphocarboxylates. The fatty acid glycinates are fatty acid amides of salts of glycine, including for example sodium cocoyl glycinate. The fatty amphocarboxylates are amphoteric surfactants including for example sodium lauroamphoacetate (i.e. sodium 2-[1-(2-hydroxyethyl)-2-undecyl-4,5-dihydroimidazol-1-ium-1-yl]acetate). Yet another example of suitable surfactants are derivatives of isethionates, including acylisethionates.

The method of disinfecting a surface according to the invention is also useful in hard surface cleaning applications. In such applications, preferred surfactants in the antimicrobial composition are nonionic surfactants, such as $C_8$-$C_{22}$, preferably $C_8$-$C_{16}$ fatty alcohol ethoxylates, comprising between 1 and 8 ethylene oxide groups when the product is in the liquid form. When the product for hard surface cleaning applications is in the solid form, surfactants are preferably selected from primary alkyl sulphates, secondary alkyl sulphonates, alkyl benzene sulphonates, ethoxylated alkyl sulphates, or alcohol ethoxylate nonionic surfactants. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Other classes of useful surfactants include cationic surfactants, such as long chain quaternary ammonium compounds and amphoteric surfactants such as betaines and alkyl dimethyl amine oxides. Suitable surfactant concentrations in liquid forms of hard surface cleaning application are generally from about from 0.5 to 10%, preferably from 1 to 5% by weight of the composition. In solid compositions, surfactant is preferably present in 5 to 40%, preferably from 10 to 30% by weight of the composition.

The antimicrobial composition for use in the method of disinfecting a surface according the invention is useful in oral care compositions e.g. In a dentifrice toothpaste or an oral rinse product. In such applications, preferred surfactants are anionic, nonionic or amphoteric in nature, preferably anionic or amphoteric. The anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear $C_{10}$-$C_{18}$ chain), and most preferably is cocoamidopropyl betaine (CAPS). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, it is highly preferred that the antimicrobial compositions include soap, alkyl sulphate or linear alkyl benzene sulphonate as the surfactants. More preferably, the one or more surfactants are selected from the group consisting of soaps, alkyl sulphates and linear alkyl benzene sulphonates.

Liquid and Solid Compositions

The antimicrobial composition may be in form of a solid, a liquid, a gel or a paste. A person skilled in the art can prepare compositions in various formats by choosing one or more carrier materials and/or surfactant. The antimicrobial compositions of the present invention are useful in methods for cleansing and care, in particular for skin cleansing and skin care. It is envisaged that the antimicrobial composition can be used as a leave-on product or a wash-off product, preferably a wash-off product. The antimicrobial composition can also be used for cleansing and care of hard surfaces such as glass, metal, plastic and the like.

A particularly preferred carrier is water. When water is the carrier, both liquid and solid compositions are possible. Different amounts of water may be preferred depending on the product format. When water is present, it is preferably present in at least 1%, more preferably at least 2%, further more preferably at least 5% by weight of the composition. When water is the carrier, a preferred liquid antimicrobial composition comprises:
  a. 0.01 to 5% by weight of thymol,
  b. 0.05 to 5% by weight of the one or more acyclic terpene alcohols,
  c. 10 to 99.9% by weight of water, and;
  d. 1 to 30% by weight of the one or more surfactants.

The liquid antimicrobial composition is useful for skin cleansing, in particular for hand wash or a face wash.

When water is the carrier, a preferred solid antimicrobial composition according to the invention comprises:
  a. 0.05 to 5% by weight of the thymol,
  b. 0.05 to 5% by weight of the one or more acyclic terpene alcohols,
  c. 5 to 30% by weight of water, and;
  d. 30 to 80% by weight of surfactant.

The solid antimicrobial composition is preferably in form of a shaped solid, more preferably a bar. The solid antimicrobial composition is particularly useful for skin cleansing in particular for hand wash or a face wash.

Such a bar-shaped solid antimicrobial composition may for instance be a soap bar. Soap bar compositions are well-known and may be similar to the following non-limiting example composition, comprising 75.6 wt-% of anhydrous sodium soap, 1.0 wt-% of glycerine, 0.5 wt-% of sodium carbonate, 0.2 wt-% of EHDP (ethane-1-hydroxy-1,1-diphosphonate) acid, 0.04 wt-% of EDTA (ethylenediaminetetraacetic acid) tetrasodium salt, 8.5 wt-% of hydrated magnesium silicate (Talc), 0.7 wt-% of sodium chloride, 0.05 wt-% of dyes, 0.75 wt-% perfume, 0.05 to 10 wt-% of antimicrobial agents including the acyclic terpene alcohols and the thymol according to the present invention, and water up to 100 wt-%.

Alternatively, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

According to another alternative, a solvent different from water is a preferred carrier. Although any solvent can be used, alcohol is a preferred solvent. Short chain alcohols—in particular ethanol, propanol, and isopropanol—are particularly preferred as carrier for an antimicrobial wipe or an antimicrobial hand sanitiser composition.

Solvents like ethanol and isopropanol generally show antimicrobial efficacy themselves. However, they are also volatile and may readily evaporate during application of the composition. Thus, their levels on the surface that is treated might even reduce until below the minimum level required for antimicrobial action, before the minimum period needed for disinfection has passed. In contrast, the thymol and the acyclic terpene alcohols according to the present invention are much less volatile and may therefore yield prolonged antimicrobial action after applying them to the skin.

Additional Ingredients

The composition may further comprise various additional ingredients known to a person skilled in the art. Such additional ingredients include but are not limited to: perfumes, pigments, preservative, emollients, sunscreens, emulsifiers, gelling agents, thickening agents, humectants (e.g., glycerine, sorbitol), sequestrants EDTA) or polymers (e.g. cellulose derivatives for structuring such as methyl cellulose)

Both thymol and some of the acyclic terpene alcohols according to the invention may contribute to the olfactory properties of the composition. Although some of these compounds might be applied for instance in perfume compositions, the present invention is directed towards antimicrobial compositions. Therefore, the composition is preferably not a perfume composition, although other perfume components can be present. Here, a perfume composition is defined as a composition comprising a plurality of olfactory components, wherein the composition is solely intended to provide a harmonious scent.

Step b of the Method for Disinfection

The method according to the first aspect of the present invention also includes the step of removing the composition from the surface. Here, removing the composition also encompasses partially removing the composition, because traces of the composition may remain on the surface. In many typical situations, including washing of the skin or hard-surface cleaning, it is acceptable or sometimes even desirable if part of the composition in particular certain active ingredients remains on the surface. Therefore, step b preferably involves removing at least 5%, more preferably at least 10%, even more preferably at least 25%, still more preferably at least 50% and yet more preferably at least 75% of the composition by weight. Preferably, the step of removing the composition comprises rinsing the surface with a suitable solvent or wiping the surface with a suitable wipe, more preferably, this step consists of rinsing the surface with a suitable solvent or wiping the surface with a suitable wipe. Alternatively, the removal step can also include evaporation of part of the composition, for example when the composition comprises volatile components, e.g. solvents.

A suitable medium for rinsing the surface is water but it could also be for example a mixture of water and alcohol. It is then rinsed preferably with sufficient amounts of water after a pre-determined period of time to remove any visible or sensory residue of the composition. Alternatively, an alcohol wipe or a water/alcohol impregnated wipe may be used to wipe the surface to be visibly free of the anti-microbial composition. The step of removing the composition (e.g. by rinsing or wiping the surface) is started less than 2 minutes, more preferably less than 1 minute, still more preferably less than 30 seconds and even more preferably less than 20 seconds after commencement of the step of applying the composition on the surface, because of the surprisingly fast antimicrobial action of the compositions according to the present invention. Even though partial microbial kill may be almost instantaneous upon application of the composition according to the invention, it is preferred that the step of removing the composition from the surface is started out at least 5 seconds, preferably at least 10 seconds, more preferably at least 15 seconds after commencement of the step of applying the composition on the surface, in order to effect optimal antimicrobial action. Combinations of these times into time intervals are preferred too. Therefore, it is particularly preferred that the step of removing the composition from the surface (i.e. step b) is started between 2 minutes and 5 seconds, more preferably between 1 minute and 10 seconds, even more preferably between 30 and 10 seconds and still more preferably between 20 and 15 seconds after commencement of the step of applying the composition on the surface (i.e. step a).

Disinfection Time

These times between applying the composition and rinsing or wiping are preferably related to the disinfection time, in order to ensure optimal cleansing and sanitising of the surface. Therefore, the invention preferably relates to a method, wherein the disinfection time T of said method is less than 300 seconds, preferably less than 120 seconds, more preferably less than 60 seconds, and even more preferably less than 15 seconds; wherein T is defined as the time that elapses from the moment of adding the composition to a microbial culture until the number of microbes per unit volume of the culture is reduced by a factor of 100 000; and wherein the initial number of microbes preferably exceeds about 100 000 000 microbes per millilitre and wherein the composition is preferably a liquid composition.

The disinfecting action of the method (as may be expressed in terms of the disinfection time T) is preferably determined according to the protocol of Example 1 as described hereinafter. This test relates to a standardised test environment in which the microbial culture is kept in suspension. A similarly suitable test is the standard suspension method described in European Standard EN 1276 with the proviso that the disinfection time is adapted to suit the above criteria as will be clear to a person skilled in the art. Alternatively, one of the test methods as described in WO 2010/046238 may for instance be applied to establish the disinfecting action.

Such test methods may preferably also be used by the skilled person to determine the optimal concentrations of the one or more acyclic terpene alcohols and the thymol in an antimicrobial composition for use in the antimicrobial method according to the present invention.

Alternatively, since the method is directed towards surface disinfection, the disinfection time may also be determined by test methods involving a surface. Therefore, the invention preferably relates to a method according to the present invention, wherein the surface disinfection time T2 of said method is less than 60 seconds; preferably less than 15 seconds, wherein T2 is defined as the time starting from the moment of applying the composition to the surface to be disinfected after which the number of microbes per unit area is reduced by a factor of 10000 (i.e. a 4 log reduction), wherein the initial number of microbes preferably exceeds $10^3$, more preferably $10^5$, and even more preferably $10^7$ microbes per square centimetre. Such tests may for instance be performed as described in WO 2010/046238, or as described in European Standards EN 13697:2001 and EN 1500:1997.

Synergistic Effect of the Invention

The inventors have surprisingly found that while one or more of the selected acyclic terpene alcohols alone or thymol alone do not individually provide the fast antimicrobial kinetic action, a combination of one or more acyclic terpene alcohols and thymol at the selective concentrations provides a synergistic antimicrobial action which is especially important in a wash off processes where the contact time of the antimicrobial actives with the surface is low, i.e. of the order of less than 5 minutes, preferably less than 2 minutes, further more preferably less than a minute and in many cases less than 15 seconds.

Synergistic Combinations of Acyclic Terpene Alcohols and Thymol

The antimicrobial action of two or more active compounds is considered additive if the combined action merely results from the addition of the effects the individual components would have in isolation. In contrast, the antimicrobial action of two or more active compounds is considered to be synergistic if the combined effect of the two or more compounds is stronger than expected based on the assumption of additivity. Without wishing to be bound by theory, it is believed that the antimicrobial action of the one compound may be enhanced by the action of the other compound and vice versa. Such enhancement may for instance originate from cooperative interplay between the mechanisms of antimicrobial action at the molecular level. Such enhanced antimicrobial action may manifest itself for instance by the fact that lower concentrations of active compounds are required to obtain complete microbial kill or alternatively, that the same extent of microbial kill is arrived at in a shorter time Whether an antimicrobial composition comprising two or more active compounds is capable of synergistic antimicrobial action may for instance be determined following the procedures and using the criteria as outlined in Example 1 below. Typically, evidence of synergistic antimicrobial action may be provided at concentrations below the minimum biocidal concentrations of each of the components when taken individually. However, it is generally believed that synergistic action, can still occur when the concentration of one or more of the active compounds is raised above its minimum biocidal concentration (when taken individually).

The antimicrobial composition preferably comprises the one or more acyclic terpene alcohols and thymol according to the invention at concentrations at which they are capable of synergistic antimicrobial action. Thus, the concentrations of the one or more acyclic terpene alcohols and of the thymol in the antimicrobial composition are preferably such that, when the composition is diluted or dissolved with a suitable medium during use, (e.g. when washing hands with water and a composition according to the invention) the concentration in the diluted or dissolved mixture is still sufficient to be antimicrobially efficacious. That is, to be capable of synergistic antimicrobial action, the concentrations of the one or more acyclic terpene alcohols and the thymol in the composition and ($C_{comp.alc}$, and $C_{comp.thymol}$, respectively) are preferably such that upon application, at a given concentration of the one or more acyclic terpene alcohols in the application medium ($C_{med.alc}$), the thymol is available at at least a minimum medium concentration ($C_{med.thymol}$) or vice versa (i.e. such that at a given $C_{med.thymol}$, a minimum $C_{med.alc}$ is available, sufficient to provide synergistic antimicrobial action). Here, the application medium denotes the medium in which the antimicrobial action desirably takes place. For example, in personal care applications like hand-washing, the composition may be a solid soap bar, in that case, $C_{comp}$ refers to the concentration of the component in the soap bar, whereas $C_{med}$ refers to the concentration in the lather. The minimum and optimum concentrations may for instance be determined by a protocol as described for Example 1 or by one of the standards as detailed below. It is generally preferred that the concentrations of the one or more acyclic terpene alcohols and the thymol in the composition applied in the methodd according to the invention are equal to or higher than the optimal concentrations in the application medium, because in many typical applications, the composition is either used pure or is diluted to form the application medium.

Surprisingly, the synergy between the acyclic terpene alcohols and thymol in compositions applied in the method according to the invention, occurs over a wide range of concentrations and concentration ratios. Depending on factors including the type of antimicrobial composition, its intended application (for instance a hard surface cleaner, a skin cleanser, or a hand sanitiser) different concentration ranges and ratios will be preferred.

Thus, when for instance antimicrobial action against *E. Coli* is desired, the data of Example 1 may be used to determine preferable medium concentrations $C_{med}$. For example, in case complete microbial inactivation is desired in the particular medium of Example 1 and if the acyclic terpene alcohol is geraniol, and $C_{med.alc}$ is selected as 0.0125% (w/v), $C_{med.thymol}$ preferably is at least 0.025% (w/v) and vice versa.

Alternatively, the desired antimicrobial effect may be obtained by selecting a ratio of the respective concentrations of the one or more acyclic terpene alcohols and the thymol. In view of the above-described considerations regarding the intended antimicrobial efficacy and other considerations, including for instance sensory properties, solubility, economic considerations, a concentration ratio of thymol to acyclic terpene alcohols larger than one is preferred in some applications, whereas a concentration ratio of thymol to acyclic terpene alcohols smaller than one is preferred in others, whereby the concentrations are expressed in %-wt.

Thus, in case a concentration ratio of thymol to acyclic terpene alcohols smaller than one is desired, then the antimicrobial composition preferably comprises the one or more acyclic terpene alcohols and thymol in a concentration ratio (thymol:acyclic terpene alcohols) of between 1:2 and 1:12, wherein the concentration is expressed as weight percent.

Alternatively, in case a concentration ratio of thymol to acyclic terpene alcohol larger than one is desired, then the antimicrobial composition according to the invention preferably comprises the one or more acyclic terpene alcohols and acyclic terpene alcohols in a concentration ratio as specified hereinbelow.

In a preferred embodiment of the invention, the synergistic antimicrobial composition comprises thymol and (+/−)-linalool. Preferably, a weight ratio of thymol to (+/−)-linalool is from 1/0.08 to 1/2.5, preferably from 1/0.25 to 1/2.5.

In a preferred embodiment of the invention, the synergistic antimicrobial composition comprises thympl and geraniol. Preferably, a weight ratio of thymol, to geraniol is from 1/0.08 to 1/33.

In a preferred embodiment of the invention, the synergistic antimicrobial composition comprises thymol and nerd. Preferably, a weight ratio of thymol to nerd is from 1/0.06 to 1/31, preferably from 1/0.06 to 1/0.17 or 1/0.25 to 1/31, preferably from 1/0.25 to 1/31, preferably from 1/2.5 to 1/31.

A further additional advantage of the present invention is that it is observed that treatment of a surface by means of the method of disinfection with a composition comprising one or more acyclic terpene alcohols and thymol, surprisingly enables continued protection of the surface against growth of microbes for a substantial period of time thereafter.

Effect of Including Surfactant

Favourably, compositions suitable in wash off processes as described above include a surfactant for the cleaning action. To the further surprise of the inventors, while the surfactant alone does not provide the fast antimicrobial kill at the concentration present in wash off processes, it provides for further improvement in extent of reduction in viable microbial counts on the surface in the short period of time when surfaces are washed with a composition comprising one or more acyclic terpene alcohols, thymol and additionally surfactant. Thus, while surfactant is generally known to be responsible for washing off dirt and also antimicrobial actives used in the composition, in the present invention, it provides a highly useful additional benefit in that it enhances the reduction of viable microbial count in a composition comprising a combination of acyclic terpene alcohols and thymol alone.

However, it was surprisingly found that certain surfactants may reduce the activity of antimicrobial agents. This may happen for instance with cocoyl glycinate and lauroamphoacetate. Generally, surfactants are required in cleaning compositions to obtain good cleaning results. Since it is inter aha an object of this invention to provide antimicrobial cleaning compositions, it therefore also is an object of this invention to provide acyclic terpene alcohols capable of enhanced antimicrobial action upon combination with thymol in the presence of such surfactants. It was found that in particular linalool and geraniol show enhanced antimicrobial action in combination with thymol. Therefore the composition according to the invention preferably comprises one or more acyclic terpene alcohols selected from linalool and geraniol. More specifically, it is preferred that in case the composition according to the invention comprises a surfactant selected from cocoyl glycinate and lauroamphoacetate, the acyclic terpene alcohol is selected from linalool and geraniol, and more preferably the acyclic terpene alcohol is geraniol.

Use According to the Invention

The invention preferably provides for non-therapeutic benefits. Thus, for instance, the invention relates to use of an antimicrobial composition as specified in the first aspect of the invention to the present invention for faster reduction in viable microbial count, Thus, according to the second aspect of the invention, there is provided use of a composition for improved hygiene, whereby the composition comprises
  i. 0.001 to 5% by weight of thymol,
  ii. 0.001 to 5% by weight of one Or more acyclic terpene alcohols, and
  iii. a carrier; and
wherein the one or more acyclic terpene alcohols have the following structure,

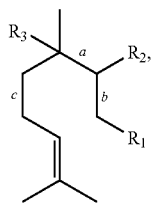

wherein
  the bonds (a), (b) and (c) are single or double bonds, whereby at most one of the bonds (a), (b) and (c) is a double bond, and whereby said double bond is not adjacent to the hydroxy group, and
  $R_1$, $R_2$ and $R_3$ are selected from hydrogen and hydroxy, whereby exactly one of $R_1$, $R_2$ and $R_3$ is hydroxy, with the proviso that $R_3$ is absent if bond (a) is a double bond.

The preferences specified for the composition applied in the first aspect of the invention also apply to the composition that is used according to the second aspect of the invention.

Such use relates for example to use of an antimicrobial composition comprising the one or more acyclic terpene alcohols, thymol and a carrier, as described above, for reduction in viable microbial count, preferably fast reduction of viable microbial count.

Thus, such use preferably is use in a method for disinfection. Fast reduction in viable microbial count therefore preferably relates to use for disinfection whereby the disinfection time is less than 300 seconds, preferably less than 120 seconds, more preferably less than 60 seconds, and even more preferably less than 15 seconds. Here, the disinfection is preferably defined similar to the disinfection times T and T2 as described above.

Thus, there is provided use of a composition according to the invention for improved hygiene of surfaces of the human body. Such surfaces include e.g. skin, hands and the oral cavity. According to a preferred aspect the invention relates to use of a composition according to the invention for improved hand hygiene. According to another preferred aspect, the invention relates to use of a composition according to the invention for improved oral hygiene.

The microbicide compositions of the present invention can be used to inhibit the growth of microorganisms by introducing a microbicidally effective amount of the compositions onto, into or at a locus subject to attack. For instance, in the field of institutional and industrial applications, suitable led include, for example: industrial process water including electrocoat deposition systems, cooling towers and air washers; gas scrubbers; wastewater treatment; ornamental fountains; reverse osmosis filtration; ultrafiltration; ballast water; evaporative condensers and heat exchangers; pulp and paper processing fluids and additives; mineral slurries; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household and institutional products used in restaurants, healthcare facilities, schools, food processing facilities and farms including, cleaners, sanitizers and disinfectants, wipes, soaps, detergents, floor polishes and laundry rinse water; cosmetics; toiletries; shampoos; metalworking fluids; conveyor lubricants; hydraulic fluids; leather and leather processing products; textiles; textile and textile processing products; wood and wood processing products, such as plywood, chipboard, wallboard, flakeboard, laminated beams, oriented strandboard, hardboard, and particleboard; oil and gas processing fluids such as injection fluids, fracture fluids, drilling muds and produced water; fuel transportation and storage systems; agriculture adjuvant preservation; surfactant preservation; medical devices; diagnostic reagent preservation; food preservation, such as plastic or paper food wrap; food, beverage, and industrial process pasteurizes; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives (such as ceramic adhesives), carpet backing adhesives, photographic chemicals, printing fluids, household and institutional products such as cleaners, sanitizers, disinfectants, wipes, cosmetics, toiletries, shampoos, soaps, detergents, floor polishes, launch), rinse water, metal working fluids, textile products, wood and wood products, agriculture adjuvant preservation, surfactant preservation, diagnostic reagent preservation, food preservation, food, beverage, and industrial process pasteurizers and oil and gas processing fluids.

Fields of Use

The composition according to the invention can in view of the above be applied for disinfection, reduction in viable microbial count or improved hygiene, especially at a surface. In preferred embodiments, the composition is particularly suited for application to the skin. For example, a surface like the hands, face, body, or the oral cavity can suitably be contacted with the composition of the invention. In other preferred embodiments, the surface is any hard surface. Typically, such hard surfaces are surfaces that commonly require cleaning and often also require sanitisation or disinfection.

Such surfaces can be found in many household or industrial environments, and can include for example kitchen and bathroom surfaces, table tops, floors, walls, windows, utensils, cutlery, and crockery. Such surfaces can be made from many different materials, for instance plastics, wood, metal, ceramics, glass, concrete, marble, and painted surfaces. In other preferred embodiments, the compositions can be used for such disinfection, reduction in viable microbial count or improved hygiene at loci other than the surfaces as described hereinbefore.

In preferred embodiments, the invention relates to compositions according to the invention for use as or incorporation in home care products and personal care products. More preferably, this embodiment of the invention relates to a composition according to the invention which is a home care product or a personal care product.

A "home care product" is a product for the treatment, cleaning, caring or conditioning of the home or any of its contents. The foregoing includes, but is not limited to compositions, products, or combinations thereof relating to or having use or application in the treatment, cleaning, cleansing, caring or conditioning of surfaces, furniture and atmosphere of the home and household contents, such as clothes, fabrics and/or cloth fibres and the manufacture of all of the foregoing products. A "personal care product" is a product for the treatment, cleaning, caring or conditioning of the person. The foregoing includes, but is not limited to, chemicals, compositions, products, or combinations thereof relating to or having use or application in the treatment, cleaning, cleansing or conditioning of the person (including in particular the skin, hair and oral cavity), and the manufacture of all the foregoing. Home care products and personal care products are for example products marketed under mass market brands, non-limiting examples being soap bars, deodorants, shampoos, and home surface sanitisers/disinfectants.

Another preferred embodiment of the invention relates to compositions according to the invention for use as or incorporation in industrial and/or institutional products. More preferably, this embodiment of the invention relates to a composition according to the invention which is an industrial and/or an institutional product. Industrial and institutional products are for example products being marketed under professional brands, non-limiting examples being for industrial, institutional, janitorial, and medical cleaning, cleaning-in-place, food services, veterinary, and agricultural products. Industrial and/or institutional products also include products for cleaning of the person (such as hand sanitisers) for medical offices, hospitals and/or other institutions.

In another preferred embodiment, the invention also relates to a method or use according to the invention involving home care products or personal care products. For example, the method according to the invention—which comprises application of a composition according to the invention in step a—can be a method wherein that composition is a composition for use as or incorporation in home care products and personal care products as described hereinabove. Similarly, in another preferred embodiment, the invention also relates to a method or use according to the invention involving industrial and/or institutional products. For example, the method according to the invention which comprises application of a composition according to the invention in step a—can be a method wherein that composition is a composition for use as or incorporation in industrial and/or institutional products as described hereinabove.

Products and/or methods for use in the home care or personal care field are generally distinct from products and/or methods for use in the industrial and/or institutional field. Thus, for example, a product that is marketed as a home or personal care product will generally not be marketed as a product for industrial and/or institutional use and vice versa. Therefore, certain embodiments of the present invention, when carried forth into practice, will relate to the one field, but not the other.

EXAMPLES

The invention is illustrated by the following nonlimiting examples.

Example 1

Assessment of Antimicrobial Efficacy

Materials

Acyclic terpene alcohols were purchased as fine chemicals from suppliers such as Sigma Aldrich, Alfa Aesar and TCI Fine Chemicals.

Thymol was purchased as 99.5% pure fine chemical grade (ex Sigma Aldrich). A terpineol mixture comprising cc 88 wt-% of (S)-alpha-terpineol, and 12 wt-% of gamma-terpineol was purchased from Sigma Aldrich and is referred to below as alpha-terpineol or terpineol unless specified otherwise.

General Method for Assessment of Antimicrobial Synergy

The efficacies of antimicrobial agents can be usefully compared by determining the Minimum Biocidal Concentration (MBC). The MBC is defined as the lowest absolute concentration of the particular active that provides complete kill (zero bacterial growth).

The differing behaviours of inhibitory antimicrobials in isolation and mixtures have been widely explored using the concept of the Fractional Concentration and Fractional Inhibitory Concentration (FIC). See for instance JRW Lambert and R Lambert, *J. Appl. Microbiol* 95, 734 (2003); T. Jadavji, C G Prober and R Cheung, *Antimicrobial Agents end Chemotherapy* 26, 91 (1984), and WO 2004/006876. These parameters can be defined as follows:

$$FC \text{ (component } a) = \frac{\text{Concentration of component } a \text{ tested in the mixture}}{MIC \text{ (component } a \text{ tested as a single active)}}$$

$$FIC \text{ (component } a) = \frac{MIC \text{ (component } a \text{ tested in the mixture)}}{MIC \text{ (component } a \text{ tested as a single active)}}$$

By analogy the Fractional Biocidal Concentration (FBC) is given by:

$$FBC \text{ (component } a) = \frac{MBC \text{ (component } a \text{ tested in the mixture)}}{MBC \text{ (component } a \text{ tested as a single active)}}$$

The interactions between antimicrobials can be additive, synergistic or possibly antagonistic depending on whether the efficacy of the combination is equivalent to, greater than or less than that obtained for the same total concentration of the individual components when tested alone.

These relationships can be expressed mathematically by summing the fractional MBC values for all the components present in the mixture to give the "fractional biocidal index":

$$\Sigma FBC = FBC_{(component\ 1)} + FBC_{(component\ 2)} + FBC_{(component\ 3)} + \ldots \text{etc}$$

such that

ΣFBC≥1 corresponds to additive or antagonistic bactericidal activity

ΣFBC<1 corresponds to synergistic bactericidal activity

Experimental Method

Antimicrobial efficacy is tested against a representative pathogenic bacterial organism, Gram negative *Escherichia coli*, Concentrations of actives are expressed in terms of the percentage weight/volume (% w/v) throughout Example 1.

Bacterial Stock

An overnight culture of *Escherichia coli* (10536 strain) was prepared in 50 ml total volume of TSB broth, grown for ca, 18 hrs at 37*C and shaken at 150 rpm. 1 ml of this overnight *E. coli* culture was transferred to 50 ml of fresh TSB broth and incubated at 37° C. at 150 rpm for ca. 4 hours. This culture was separated into equal volumes and centrifuged at 4000 rpm for 15 minutes, washed with sterile saline (0.85% NaCl), centrifuged once more and re-suspended in saline to give a final concentration of 0.8 $OD_{620}$ equivalent to about $10^8$ cells per millilitre for this particular organism. Here, $OD_{620}$ indicates the absorbance of a sample in a cuvette of 1.0 cm path length at a wavelength of 620 nm. This bacterial stock was used for assaying against antimicrobial actives (in triplicate).

Protocol

The following assay describes the testing of 8 materials using 6 dilutions across half of a 96-well micro titre plate (MTP). Using this approach it is possible to assay 16 actives (without replicates) with one full dilution plate, replicating this set up in two halves of the plate columns, 1-6 and 7-12.

1 M solutions of the test actives were prepared in dimethylsulphoxide (DMSO) Stock solutions of the actives at 1.11 times the desired final concentration were prepared by diluting the DMSO solutions in water, so that for example a 0.89% w/v solution was prepared for a desired "in test" concentration of 0.8% w/v in order to allow for the further dilution of the active when the bacterial suspension is added (dilution from 270 µl to 300 µl), as described below.

Aliquots (270 µl) of the materials at 1.11 times the final concentration were dispensed into the wells of the MTP along one column (A1~H1). This MTP was labelled as the "Screening plate".

In another MTP, labelled as the "Dilution plate", 270 µl of D/E neutralising solution from DIFCO Composition was added to column 1. The composition of the neutralising solution was as follows: pancreatic digest of casein, 5.0 g/L; Yeast Extract, 2.5 g/L; Dextrose, 10 g/L, sodium thioglycollate, 1.0 g/L, sodium thiosulphate, 6.0 g/L; sodium bisulphite, 2.5 g/L; Polysorbate 80, 5.0 g/L; lecithin 7.0 g/L; bromocresol purple, 0.02 g/L with a pH in the range 7.6±0.2.

270 µl of tryptone diluent solution was added to all the remaining wells of the Dilution MTP (columns 2-6).

Bacterial stock (30 µl) was then added to the prepared 270 µl of the solution of actives in the Screening Plate and mixed, using a multichannel pipette with 8 tips Co aspirate and dispense the same volume of bacterial stock in parallel to 8 wells in rows A-H. After a contact time of 15 seconds, the mixtures were quenched by transferring 30 µl volumes of the mixtures into the 270 µl D/E neutralising solution in the prepared dilution plate, using aspiration to mix. After exactly 5 minutes in the D/E neutralising solution, 30 µl volumes were transferred from column 1 to column 2 of the Dilution MTP and mixed, before transferring further 30 µl volumes from column 2 into column 3. This process was repeated serially diluting the bacteria across the plate to column 6.

30 µl volumes from each well in the Dilution MTP were transferred onto pre-labelled segment of Tryptone Soya Agar (TSA) plates starting from the lowest bacterial concentration (highest dilution, column 6) to the highest bacterial concentration (column 1). The ISA plates were allowed to stand for ca. 2 hours so that the 30 µl inocula spots could dry and the plates were then inverted and incubated overnight at 37° C. before enumerating the bacterial colonies at the labelled dilutions to determine the effects of the actives on bacterial growth.

Calculation of Results

Mean bacterial survival numbers $N_{MBS}$ (expressed in Log CFU/ml) are obtained by first determining the segment of the TSA plate where the number of bacterial colonies is countable. From the colony number in this segment, $N_{MBS}$ is calculated by the formula;

$$N_{MBS} = \log\{N_{col} \cdot 10^{DF} \cdot 100/3\}$$

Here, $N_{col}$ is the colony count, and DF is the dilution factor taken from the MTP-well corresponding to the TSA plate segment (i.e. DF may range from 1 for the quench, to 6 for the highest dilution). The factor 100/3 is a conversion factor from the volume of the inocula spot to one millilitre.

Every assay test was performed in triplicate. The reported mean bacterial survival results are the average of such a triplet, the error is the corresponding standard deviation.

Thus, a value of $N_{MBS}$ of about 7 corresponds to a count of about 3 colonies from the fifth dilution well, i.e. with DF=5. Such a count of about 7 is generally observed when bacteria are exposed to non-biocidal materials. In case no surviving colonies are observed in any segment of the TSA plate, this is interpreted as complete kill and a value of $N_{MBS}=0$ is reported.

Validation

All test results were validated by running every test assay in parallel with four control experiments on the same MTP. All control experiments are executed exactly according to the above protocol, but with the following active ingredients:

A 0.025%(w/v) thymol
B 0.15% (w/v) alpha-terpineol
C 0.025% (w/v) thymol+0.15% (w/v) alpha-terpineol
D no active component The control experiments A, B and D validate a test assay by not showing bacterial kill, whereas control experiment C, comprising a synergistic combination of thymol and alpha-terpineol according to WO 2010/046238 A1 validates a test assay by showing complete bacterial kill.

A reference experiment according to the above protocol, but without active component, showed that DMSO does not affect bacterial growth at the concentrations present in the test solutions in this protocol (<5% (w/v)), as can be seen in Table 2

TABLE 2

| DMSO in water (% w/v) | Mean bacterial survival [log CFU/ml] | Standard deviation |
|---|---|---|
| 4.5 | 8.2 | 0.1 |
| 3.6 | 8.4 | 0.2 |
| 2.7 | 8.2 | 0.1 |
| 1.8 | 8.5 | 0.2 |
| 0.9 | 8.6 | 0.1 |
| 0.0 | 8.5 | 0.1 |

Results

The above method was applied to asses the antibacterial efficacy of the acyclic terpene alcohols according to the invention. Table 3 shows the antibacterial activities of the acyclic terpene alcohols, both alone and in conjunction with thymol.

TABLE 3

Antibacterial activities of terpineol, and acyclic terpene alcohols alone and in combination with thymol

| Example | Thymol concentration $C_{thymol}$ (% w/v) | Concentration of terpineol/acyclic terpene alcohols/reference compounds $C_{alc}$ (% w/v) | $N_{MBS}{}^a$ | S.D.$^b$ |
|---|---|---|---|---|
| 1:1* | 0.075 | 0 | 0 | 0 |
| 1:2* | 0.05 | 0 | 0 | 0 |
| 1:3* | 0.025 | 0 | 7.63 | 0.09 |
| 1:4* | 0 | 0.5% alpha-terpineol | 0 | 0 |
| 1:5* | 0 | 0.4% alpha-terpineol | 0 | 0 |
| 1:6* | 0 | 0.3% alpha-terpineol | 7 | 0.2 |
| 1:7* | 0 | 0.15% alpha-terpineol | 7 | 0.2 |
| 1:8* | 0 | 0.4% (+/−)-linalool | 0 | 0 |
| 1:9* | 0 | 0.3% (+/−)-linalool | 7.6 | 0.2 |
| 1:10 | 0.025 | 0.15% (−)-linalool | 0 | 0 |
| 1:11 | 0.025 | 0.10% (−)-linalool | 0 | 0 |
| 1:12* | 0 | 0.4 (+/−)-linalool | 0 | 0 |
| 1:13* | 0 | 0.3% (+/−)-linalool | 7.6 | 0.1 |
| 1:14 | 0.025 | 0.15% (+/−)-linalool | 0 | 0 |
| 1:15 | 0.025 | 0.10% (+/−)-linalool | 0 | 0 |
| 1:16* | 0 | 0.0375% geraniol | 0 | 0 |
| 1:17* | 0 | 0.01875% geraniol | 7.7 | 0.2 |
| 1:18 | 0.025 | 0.0125% geraniol | 0 | 0 |
| 1:19* | 0.05 | 0.05% dihydromyrcenol$^c$ | 7.6 | 0.1 |
| 1:20* | 0.025 | 0.15% ocimene$^d$ | 6.9 | 0.5 |
| 1:21* | 0 | 0.5% tetrahydrolinalool$^e$ | 7.69 | 0.26 |
| 1:22* | 0 | 0.4% tetrahydrolinalool | 7.66 | 0.17 |
| 1:23* | 0 | 0.3% tetrahydrolinalool | 7.65 | 0.19 |
| 1:24* | 0 | 0.15% tetrahydrolinalool | 7.70 | 0.07 |
| 1:25* | 0.025% | 0.4% tetrahydrolinalool | 7.54 | 0.16 |
| 1:26* | 0.025% | 0.3% tetrahydrolinalool | 7.71 | 0.17 |
| 1:27* | 0.025% | 0.15% tetrahydrolinalool | 7.61 | 0.04 |
| 1:28* | 0 | 0.5% tetrahydrogeraniol$^f$ | 7.69 | 0.26 |
| 1:29* | 0 | 0.4% tetrahydrogeraniol | 7.66 | 0.17 |
| 1:30* | 0 | 0.3% tetrahydrogeraniol | 7.65 | 0.19 |
| 1:31* | 0 | 0.15% tetrahydrogeraniol | 7.7 | 0.07 |
| 1:32* | 0.025% | 0.4% tetrahydrogeraniol | 7.60 | 7.87 |
| 1:33* | 0.025% | 0.3% tetrahydrogeraniol | 7.65 | 7.78 |
| 1:34* | 0.025% | 0.15% tetrahydrogeraniol | 7.66 | 7.80 |

*Examples marked with an asterisk (*) are comparative examples
$^a N_{MBS}$ in [log CFU/ml]
$^b$ S.D. = standard deviation
$^c$ dihydromyrcenol = 2,6-dimethyloct-7-en-2-ol
$^d$ ocimene = 3,7-dimethyl-1,3,6-octatriene
$^e$ tetrahydrolinalool = 3,7-dimethyl-1-octanol
$^f$ tetrahydrogeraniol = 3,7-dimethyl-3-octanol

Comparative Examples

Determination of the parameter ΣFBC, which is used as measure of the synergistic antimicrobial action of compositions according to the present invention, requires determination of the Minimum Biocidal Concentrations (MBCs) of the relevant actives first. As described above, the MBC for an active can be defined as the lowest concentration of the active that provides zero bacterial bacterial survival in the particular medium, Data for examples (1:1) to (1:3) demonstrate that the MBC value for thymol is 0.05% (w/v). For alpha-terpineol, compositions (1:4) to (1:7), show that the MBC is 0.4% w/v. The same analysis has been carried out for selected acyclic terpene alcohols and is summarised in Table 4 below. These MBC values constitute the upper boundaries to the respective MBCs in the particular medium used in these examples.

TABLE 4

Minimum biocidal concentrations of antimicrobial components

| Component | MBC (% w/v) |
|---|---|
| thymol | 0.05 |
| alpha-terpineol | 0.4 |
| (−)-linalool | 0.4 |
| (+/−)-linalool | 0.4 |
| geraniol | 0.038 |

It is clear from the data in Table 4 that linalools are efficacious antimicrobial agents. Moreover, geraniol is a more efficacious antimicrobial compound than terpineol and can be used at lower concentrations.

Synergistic Interactions

The tested combinations of the selected acyclic terpene alcohols with thymol provide complete bacterial kill in the examples. Using the MBC values listed in Table 4 above, the fractional MBC values for the components present in these mixtures and the experimental ΣFBC of the compositions can be calculated in order to discriminate between combinations providing evidence of synergistic effects, as opposed to additive biocidal effects. The results from this analysis are given in Table 5.

TABLE 5

Extent of synergistic interactions between binary compound mixtures for compositions providing complete bacterial kill

| acyclic terpene alcohol | | | | thymol | | | |
|---|---|---|---|---|---|---|---|
| compound | Ex. | MBC % (w/v) | FBC$^a$ | MBC % (w/v) | FBC$^b$ | ΣFBC | Evidence of Synergy$^c$ |
| (−)-linalool | 1:10 | 0.4 | 0.38 | 0.05 | 0.5 | 0.88 | Yes |
| (−)-linalool | 1:11 | 0.4 | 0.25 | 0.05 | 0.5 | 0.75 | Yes |
| (+/−)-linalool | 1:14 | 0.4 | 0.38 | 0.05 | 0.5 | 0.88 | Yes |
| (+/−)-linalool | 1:15 | 0.4 | 0.25 | 0.05 | 0.5 | 0.75 | Yes |
| geraniol | 1:18 | 0.4 | 0.33 | 0.05 | 0.5 | 0.83 | Yes |

$^a$ FBC of acyclic terpene alcohols: $C_{alc}/MBC_{alc}$
$^b$ FBC of thymol: $C_{thymol}/MBC_{thymol}$
$^c$ Criterion for synergy: (ΣFBC <1)

For Examples (1:10), (1:11) (1:14), (1:15) and (1:18), the ΣFBC value is below 1, thus providing evidence for synergistic interactions, according to the set criteria. Therefore, these examples show how the antimicrobial efficacy of thymol and acyclic terpene alcohols according to invention are enhanced when they are applied together. Such synergies allow for reductions in the concentrations of the antimicrobials required to achieve complete kill. For example 0.05% w/v thymol is required to achieve complete bacterial kill when tested in isolation but this can be reduced 2-fold to 0.025% when used in combination with for example 0.0125% w/v of geraniol.

Comparative Examples

The comparative examples (1:19) to (1:34) show that compositions comprising thymol and comparative compounds that are not compounds according to the present invention at concentrations comparable to those in the examples according to the invention do not give rise to fast antimicrobial action.

Example 2

In this Example, a wide range of combinations of chemicals was tested by conducting high resolution MBC assays of selected acyclic terpene alcohols in the presence of various concentrations of thymol. The materials were sourced in the same way as for Example 1. Synergy tests were conducted using standard microtiter plate assays with phosphate buffer containing 35% dipropylene glycol (DPG). High resolution MBCs were determined by adding varying amounts of microbicide to one column of a microtiter plate and doing subsequent ten-fold dilutions using an automated liquid handling system to obtain a series of endpoints ranging from 0.002% to 1% of the test compound. The MBC plate was inoculated one column at a time with the test microorganism. An aliquot of the inoculated well was transferred at 15 seconds to a plate containing a neutralizing agent (DIE Neutralizing Broth), mixed and held for 5 minutes before being transferred to a growth plate containing trypticase soy broth (TSB). The TSB plate was incubated at 37° C. and read for the presence/absence of growth at 24 hours. The lowest level tested that provided complete kill (as evidenced by lack of growth on the microtitre plate) of the test organisms in 15 seconds is defined as the minimum biocidal concentration (MBC) throughout Example 2.

The synergy of the combinations of the present invention was determined against a the same bacterium as in Example 1, *Escherichia coli* (*E. coli* ATCC #10536), at a concentration of approximately $1 \times 10^8$ bacteria per mL. This microorganism is representative of natural contaminants in many consumer and industrial applications. The plates were visually evaluated for microbial growth (turbidity) to determine the MBC after 24 hours incubation time at 37° C.

The test results for demonstration of synergy of the combinations of the present invention are shown below in Tables 6 to 8. The tables show the specific combinations of two components: results against the microorganism tested: the end-point activity in weight % measured by the MBC for the first component alone (thymol, $MBC_A$), for the second component alone (acyclic terpene alcohol, $MBC_B$), for the first component in the mixture ($C_a$) and for the second component in the mixture ($C_b$); the calculated ΣFBC value; and the range of synergistic ratios for each combination tested (first component t second component or A/B) against the particular microorganism.

Data in the table below include the range of ratios that were found to be synergistic. (Data which were collected outside of the synergistic ranges are not reported.) These data demonstrate that certain combinations of components thymol and acyclic terpene alcohols show more enhanced control over the microorganisms than would be expected if the combinations were additive rather than synergistic.

TABLE 6

First Component (A) = thymol
Second Component (B) = (+/−)-linalool

| Microorganism | $C_a$ | $C_b$ | ΣFBC | Ratio A to B |
|---|---|---|---|---|
| E. coli 10536 | 0.5 | 0 | 1.00 | |
| | 0.2 | 0.025 | 0.45 | 1 to 0.13 |
| | 0.3 | 0.025 | 0.65 | 1 to 0.08 |
| | 0.5 | 0.05 | 1.10 | 1 to 0.1 |
| | 0.3 | 0.075 | 0.75 | 1 to 0.25 |
| | 0.4 | 0.075 | 0.95 | 1 to 0.19 |
| | 0.2 | 0.1 | 0.60 | 1 to 0.5 |
| | 0.3 | 0.1 | 0.80 | 1 to 0.33 |
| | 0.1 | 0.25 | 0.70 | 1 to 2.5 |
| | 0.2 | 0.25 | 0.90 | 1 to 1.25 |
| | 0 | 0.5 | 1.00 | |

The ratios of thymol to (+/−)-linalool tested ranged from 1/0.025 to 1/350. The synergistic ratios of thymol to (+/−)-linalool range from 1/0.08 to 1/2.5.

TABLE 7

First Component (A) = thymol
Second Component (B) = geraniol

| Microorganism | $C_a$ | $C_b$ | ΣFBC | Ratio A to B |
|---|---|---|---|---|
| E. coli 10536 | 0.4 | 0 | 1.00 | |
| | 0.2 | 0.025 | 0.58 | 1 to 0.13 |
| | 0.3 | 0.025 | 0.83 | 1 to 0.08 |
| | 0.2 | 0.05 | 0.67 | 1 to 0.25 |
| | 0.3 | 0.05 | 0.92 | 1 to 0.17 |
| | 0.2 | 0.075 | 0.75 | 1 to 0.38 |
| | 0.3 | 0.1 | 1.08 | 1 to 0.33 |
| | 0.006 | 0.2 | 0.68 | 1 to 33 |
| | 0.008 | 0.2 | 0.69 | 1 to 25 |
| | 0.01 | 0.2 | 0.69 | 1 to 20 |
| | 0.02 | 0.2 | 0.72 | 1 to 10 |
| | 0.03 | 0.2 | 0.74 | 1 to 6.7 |
| | 0.04 | 0.2 | 0.77 | 1 to 5 |
| | 0.06 | 0.2 | 0.82 | 1 to 2 |
| | 0.08 | 0.2 | 0.87 | 1 to 2.5 |
| | 0.1 | 0.2 | 0.92 | 1 to 2 |
| | 0 | 0.3 | 1.00 | |

The ratios of thymol to geraniol tested ranged from 1/0.025 to 1/250. The synergistic ratios of thymol to geraniol range from 1/0.08 to 1/33.

TABLE 8

First Component (A) = thymol
Second Component (B) = nerol

| Microorganism | $C_a$ | $C_b$ | ΣFBC | Ratio A to B |
|---|---|---|---|---|
| E. coli 10536 | 0.5 | 0 | 1.00 | |
| | 0.3 | 0.025 | 0.65 | 1 to 0.08 |
| | 0.4 | 0.025 | 0.85 | 1 to 0.06 |
| | 0.2 | 0.05 | 0.50 | 1 to 0.25 |
| | 0.3 | 0.05 | 0.70 | 1 to 0.17 |
| | 0.4 | 0.05 | 0.90 | 1 to 0.13 |
| | 0.2 | 0.075 | 0.55 | 1 to 0.38 |
| | 0.3 | 0.075 | 0.75 | 1 to 0.25 |
| | 0.4 | 0.075 | 0.95 | 1 to 0.19 |
| | 0.2 | 0.1 | 0.60 | 1 to 0.5 |
| | 0.3 | 0.1 | 0.80 | 1 to 0.33 |
| | 0.008 | 0.25 | 0.52 | 1 to 31 |
| | 0.01 | 0.25 | 0.52 | 1 to 25 |
| | 0.02 | 0.25 | 0.54 | 1 to 12.5 |
| | 0.03 | 0.25 | 0.56 | 1 to 8.3 |
| | 0.04 | 0.25 | 0.58 | 1 to 6.25 |
| | 0.05 | 0.25 | 0.60 | 1 to 5 |
| | 0.06 | 0.25 | 0.62 | 1 to 4.2 |
| | 0.08 | 0.25 | 0.66 | 1 to 3.1 |
| | 0.1 | 0.25 | 0.70 | 1 to 2.5 |
| | 0.2 | 0.25 | 0.90 | 1 to 1.25 |
| | 0 | 0.5 | 1.00 | |

The ratios of thymol to nerol tested ranged from 1/0.025 to 1/350. The synergistic ratios of thymol to nerol range from 1/0.08 to 1/33.

The results of Examples 1 and 2 demonstrate that a synergistic antimicrobial effect of acyclic terpene alcohols according to the invention and thymol may be obtained over a wide range of concentrations and ratios.

Example 3

Automated Assessment of Efficacy in Surfactant Base

Sample Preparation

In these examples, the efficacy of combinations of thymol and acyclic terpene alcohols were tested in a surfactant cleansing formulation comprising 2.85% sodium cocoyl glycinate and 1.85% sodium lauroamphoacetate. This corresponds to a 50% in use dilution with water of a typical neat formulation containing 5.7% cocoyl glycinate and 3.7% % sodium lauroamphoacetate during hand washing. Solutions were prepared such that the concentrations of the surfactant components and test actives were 1.1 times the final desired concentration in order to allow for dilution with the bacterial inoculum in the test. The solutions were manually adjusted to pH 10.0 by dropwise addition of sodium hydroxide solution, as measured with a pH meter at ambient temperature. Solutions of the thymol and/or acyclic terpene alcohols were prepared at a maximum of 24 hours before testing. The same thymol and acyclic terpene alcohols were used as in Example 1.

Test Methodology

The efficacy of the combinations of the present invention was determined against the same bacterium as in Example 1, *Escherichia coli* (*E. coli*—ATCC #10536), at a concentration of approximately $1 \times 10^8$ bacteria per mL.

Tests were conducted using standard microtiter plate assays using an automated liquid handling system. 270 μl of the surfactant test solution was pipetted into each well of the microtitre plate (Nunc F Gamma irradiated 96F untreated microtitre plates of clear polystyrene) and 30 μl of the bacterial suspension was then added. After exactly 15 seconds of bacterial exposure, a 30 μl volume of bacterial cells was withdrawn and transferred to 270 μl of D/E quench solution.

After 5 minutes in the D/E quench, the optical density (OD) was measured for each plate in turn at two specific wavelengths (450 nm and 590 nm). These provide a dual check of antimicrobial activity, as the $OD_{450}$ reading is specific for the yellow colour of DIE quench when bacterial growth is observed, whereas $OD_{590}$ is specific for the initial purple colour of the D/E quench which is retained if no bacterial growth is observed. After the time zero OD measurements, plates were then incubated at 37° C. overnight (16 hours) before repeating the OD measurements. Delta OD values were calculated by subtracting the OD values at 16 hours from the initial value at time zero from those at time=16 hours. Bacterial growth is observed as an increase in $OD_{450}$ and a decrease in $OD_{590}$. To identify antibacterially efficacious systems (those preventing appreciable bacterial growth after incubation), the following threshold changes in OD readings have been adopted: if (1), $OD_{450}$ increases by less than 0.2 absorbance unit (AU) on incubation and (2), $OD_{590}$ decreases by less than 0.35 AU on incubation, Conversely, where $OD_{450}$ increases by more than 0.1 AU and $OD_{590}$ decreases by more than 0.1 AU after incubation, corresponding to a colour shift from purple to yellow, the test system allows bacterial growth and is not deemed efficacious. Four replicate measurements in the same plate have been made for each test system. The number of replicate wells showing either bacterial growth or no growth is also readily assessed by eye by following the colour change. Thymol and terpineol were tested both alone and in combination for comparison purposes.

Dose responses for individual components and binary mixtures of actives at a fixed concentration ratio were generated by sequential dilution of liquors with further surfactant solution to obtain a series of endpoints ranging from 0.2 to 0.025% of the thymol and 0.5% to 0.0625% of acyclic terpene alcohol. In each case, binary mixtures were assessed in the weight to weight ratio of thymol to acyclic terpene alcohol of 1:2.5.

TABLE 9

Antibacterial activities of acyclic terpene alcohols alone, and in combination with thymol in model surfactant solution.

| Ex. | $C_{thymol}$[a] (% w/v) | $C_{alc}$[b] (% w/v) | DeltaOD (450 nm)[c] Mean | S.D.[f] | DeltaOD (590 nm)[d] Mean | S.D.[f] | $N_{rep}$[e] out of 4 |
|---|---|---|---|---|---|---|---|
| 3:1* | 0 | 0 | −0.60 | 0.02 | 0.64 | 0.02 | 4 |
| 3:2* | 0.2% | 0 | −0.54 | 0.02 | 0.64 | 0.02 | 4 |
| 3:3* | 0.175% | 0 | −0.54 | 0.02 | 0.56 | 0.02 | 4 |
| 3:4* | 0.15% | 0 | −0.57 | 0.01 | 0.55 | 0.01 | 4 |
| 3:5* | 0.125% | 0 | −0.58 | 0.01 | 0.55 | 0.01 | 4 |
| 3:6* | 0.1% | 0 | −0.58 | 0.00 | 0.54 | 0.02 | 4 |
| 3:7* | 0.075% | 0 | −0.59 | 0.01 | 0.54 | 0.01 | 4 |
| 3:8* | 0.05% | 0 | −0.58 | 0.03 | 0.55 | 0.01 | 4 |
| 3:9* | 0.025% | 0 | −0.55 | 0.01 | 0.65 | 0.02 | 4 |
| 3:10* | 0 | 0.5% (+/−)Linalool | −0.48 | 0.02 | 0.65 | 0.03 | 4 |
| 3:11* | 0 | 0.4% (+/−)Linalool | −0.50 | 0.02 | 0.57 | 0.03 | 4 |
| 3:12* | 0 | 0.35% (+/−)Linalool | −0.50 | 0.01 | 0.58 | 0.02 | 4 |
| 3:13* | 0 | 0.3% (+/−)Linalool | −0.52 | 0.01 | 0.56 | 0.01 | 4 |
| 3:14* | 0 | 0.25% (+/−)Linalool | −0.56 | 0.02 | 0.55 | 0.01 | 4 |
| 3:15* | 0 | 0.2% (+/−)Linalool | −0.57 | 0.02 | 0.55 | 0.01 | 4 |
| 3:16* | 0 | 0.15% (+/−)Linalool | −0.59 | 0.02 | 0.54 | 0.01 | 4 |
| 3:17 | 0.2% | 0.5% (+/−)Linalool | 0.24 | 0.03 | 0.26 | 0.03 | 0 |
| 3:18 | 0.175% | 0.4375% (+/−)Linalool | 0.13 | 0.02 | 0.15 | 0.02 | 0 |
| 3:19 | 0.15% | 0.375% (+/−)Linalool | 0.09 | 0.02 | 0.13 | 0.02 | 0 |
| 3:20 | 0.125% | 0.3125% (+/−)Linalool | −0.24 | 0.33 | 0.31 | 0.28 | 2 |

TABLE 9-continued

Antibacterial activities of acyclic terpene alcohols alone, and in combination with thymol in model surfactant solution.

| Ex. | $C_{thymol}{}^{(a)}$ (% w/v) | $C_{alc}{}^{(b)}$ (% w/v) | DeltaOD (450 nm)$^{(c)}$ Mean | S.D.$^{(f)}$ | DeltaOD (590 nm)$^{(d)}$ Mean | S.D$^{(f)}$ | $N_{rep}{}^{(e)}$ out of 4 |
|---|---|---|---|---|---|---|---|
| 3:21 | 0.1% | 0.25% (+/−)Linalool | −0.53 | 0.02 | 0.56 | 0.01 | 4 |
| 3:22 | 0.075% | 0.1875% (+/−)Linalool | −0.55 | 0.01 | 0.56 | 0.01 | 4 |

*Examples marked with an asterisk (*) are comparative examples
$^{(a)}$Concentration of thymol
$^{(b)}$Concentration of acyclic terpene alcohol as specified
$^{(c)}$DeltaOD (450 nm) = OD$_{450}$ (time = 16 hours) − OD$_{450}$ (time zero)
$^{(d)}$DeltaOD (590 nm) = OD$_{590}$ (time = 16 hours) − OD$_{590}$ (time zero)
$^{(e)}$N$_{rep}$ = No. of replicates showing growth (out of 4)
$^{(f)}$S.D. = standard deviation

TABLE 10

Antibacterial activities of acyclic terpene alcohols alone, and in combination with thymol in model surfactant solution.

| Ex. | $C_{thymol}{}^{(a)}$ (% w/v) | $C_{alc}{}^{(b)}$ (% w/v) | DeltaOD (450 nm)$^{(c)}$ Mean | S.D.$^{(f)}$ | DeltaOD (590 nm)$^{(d)}$ Mean | S.D$^{(f)}$ | $N_{rep}{}^{(e)}$ out of 3 |
|---|---|---|---|---|---|---|---|
| 3:23* | 0 | 0.5% Geraniol | −0.58 | 0.01 | 0.59 | 0.02 | 3 |
| 3:24* | 0 | 0.3125% Geraniol | −0.64 | 0.01 | 0.52 | 0.02 | 3 |
| 3:25* | 0 | 0.15625% Geraniol | −0.69 | 0.02 | 0.49 | 0.01 | 3 |
| 3:26* | 0 | 0.0875% Geraniol | −0.70 | 0.02 | 0.48 | 0.01 | 3 |
| 3:27 | 0.1% | 0.25% Geraniol | 0.24 | 0.01 | 0.20 | 0.18 | 0 |
| 3:28 | 0.08% | 0.2% Geraniol | 0.10 | 0.06 | 0.17 | 0.08 | 0 |
| 3:29 | 0.06% | 0.15% Geraniol | −0.66 | 0.03 | 0.54 | 0.51 | 3 |
| 3:30 | 0.05% | 0.125% Geraniol | −0.64 | 0.00 | 0.52 | 0.51 | 3 |

*Examples marked with an asterisk (*) are comparative examples
$^{(a)}$Concentration of thymol
$^{(b)}$Concentration of acyclic terpene alcohol as specified
$^{(c)}$DeltaOD (450 nm) = OD$_{450}$ (time = 16 hours) − OD$_{450}$ (time zero)
$^{(d)}$DeltaOD (590 nm) = OD$_{590}$ (time = 16 hours) − OD$_{590}$ (time zero)
$^{(e)}$N$_{rep}$ = No. of replicates showing growth (out of 3)
$^{(f)}$S.D. = standard deviation

TABLE 11

Minimum biocidal concentrations of antimicrobial components in 2.85% sodium cocoyl glycinate + 1.85% sodium lauroamphoacetate solution at pH 10

| Component | MBC (% w/v) |
|---|---|
| Thymol | >0.2 |
| (+/−)-linalool | >0.5 |
| geraniol | >0.5 |

TABLE 12

Extent tryf synergistic interactions between binary compound mixtures for compositions providing complete bacterial kill

| MBC compound | Ex. | % (w/v) | FBC$^a$ | thymol MBC % (w/v) | FBC$^b$ | ΣFBC | Evidence of Synergy$^c$ |
|---|---|---|---|---|---|---|---|
| geraniol | 3:28 | 0.5 | 0.4 | 0.2 | 0.4 | 0.8 | Yes |

$^a$FBC of acyclic terpene alcohol: $C_{alc}$/MBC$_{alc}$
$^b$FBC of thymol: $C_{thymol}$/MBC$_{thymol}$
$^c$Criterion for synergy: (ΣFBC <1)

Results

The surfactants used are not themselves antimicrobially active against *E. coli* at the concentrations employed as shown by the results of Ex. (3:1) in Table 9. Thus, any antimicrobial efficacy can be ascribed to the acyclic terpene alcohols and/or thymol. Table 11 presents MBC-values determined similarly as described for Example 1. The tested compounds have an MBC higher than the highest tested concentrations, in the presence of the specified surfactants.

The results of Tables 9 and 10 demonstrate that (+/−)-linalool and geraniol show 15 second bactericidal efficacy (complete kill in all 4 or 3 replicates, respectively) against *E. coli* when tested in combination with thymol at concentrations lower than their MBC in the same surfactant formulation (comprising car oyl glycinate and lauroamphoacetate). In particular, Example (3:28) shows that geraniol and thymol provide synergistic; antimicrobial action against *E. coli* in the presence of cocoyl glycinate and lauroamphoacetate, as shown in Table 12

Thus, it was found that acyclic terpene alcohols according to the invention and in particular linalool and go anal show enhanced antimicrobial action in combination with terpineol in the presence of surfactant, in particular cocoyl glycinate and lauroamphoacetate.

The invention claimed is:
1. A synergistic microbicidal composition comprising:
(a) thymol; and
(b) geraniol;
wherein a weight ratio of thymol to geraniol is from 1:0.08 to 1:0.25, 1:2 to 1:6.7 or 1:10 to 1:25.
2. A synergistic microbicidal composition comprising:
(a) thymol; and
(b) (+/−)-linalool;
wherein a weight ratio of thymol to (+/−)-linalool is from 1:0.25 to 1:0.33 or 1:1.25 to 1:2.5.

3. A synergistic microbicidal composition comprising:
(a) thymol; and
(b) nerol;
wherein a weight ratio of thymol to nerol is from 1:0.25 to 1:31.

* * * * *